US 6,633,627 B2

(12) United States Patent
Horiuchi (10) Patent No.: US 6,633,627 B2
(45) Date of Patent: Oct. 14, 2003

(54) X-RAY CT SYSTEM, GANTRY APPARATUS, CONSOLE TERMINAL, METHOD OF CONTROLLING THEM, AND STORAGE MEDIUM

(75) Inventor: Tetsuya Horiuchi, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 205 days.

(21) Appl. No.: 09/919,164

(22) Filed: Jul. 31, 2001

(65) Prior Publication Data

US 2002/0037067 A1 Mar. 28, 2002

(30) Foreign Application Priority Data

Sep. 28, 2000 (JP) ........................................ 2000-296913

(51) Int. Cl.[7] .................................................. G21K 3/00
(52) U.S. Cl. ............................ 378/156; 378/4; 378/157
(58) Field of Search ................................ 378/156, 157, 378/158, 145, 148

(56) References Cited

U.S. PATENT DOCUMENTS

| | | | | |
|---|---|---|---|---|
| 4,744,099 A | * | 5/1988 | Huettenrauch et al. | ..... 378/157 |
| 5,552,606 A | * | 9/1996 | Jones et al. | ............ 250/363.04 |
| 5,867,553 A | | 2/1999 | Gordon et al. | |
| 6,307,918 B1 | | 10/2001 | Toth et al. | |

FOREIGN PATENT DOCUMENTS

| | | |
|---|---|---|
| EP | 0981999 | 3/2000 |
| WO | 9716721 | 5/1997 |

* cited by examiner

Primary Examiner—Louis Arana
(74) Attorney, Agent, or Firm—Moonray Kojima (57) ABSTRACT

In order to obtain an X-ray tomographic image with high quality while minimizing the exposed dose to a subject by employing the most suitable filter according to the region of the subject to be scanned, a filter unit 6 having filters 6a–6c having different transmission properties are provided below an X-ray tube 4 in a gantry apparatus. To obtain an X-ray tomographic image, upon determining the scan region of the subject, a motor 7 is driven to position one of the filters corresponding to the scan region just below the X-ray tube 4 for employing the filter, and X-rays are applied to the subject through the filter.

17 Claims, 7 Drawing Sheets

|  | Large | Medium | Small |
|---|---|---|---|
| Head | $f_3$ | $f_2$ | $f_1$ |
| Thorax | $f_6$ | $f_5$ | $f_4$ |
| Abdomen | $f_9$ | $f_8$ | $f_7$ |

X-RAY CT SYSTEM, GANTRY APPARATUS, CONSOLE TERMINAL, METHOD OF CONTROLLING THEM, AND STORAGE MEDIUM

BACKGROUND OF THE INVENTION

The present invention relates to an X-ray CT system, gantry apparatus, console terminal, method of controlling them, an-d storage medium, for obtaining an X-ray tomographic image of a subject by X-ray irradiation.

An X-ray CT (computed tomography) system and apparatus comprises, in a broad classification, an apparatus of a toroidal shape having a cavity portion (generally referred to as a gantry apparatus), an operating console for supplying several types of control signals to the gantry apparatus and reconstructing an X-ray tomographic image based on signals (data) obtained from the gantry apparatus for display, and a carrier apparatus for supporting a subject (human subject) fixed within the cavity portion of the gantry apparatus and carrying the subject toward the cavity portion.

The gantry apparatus comprises a rotating section incorporating therein an X-ray generating source (X-ray tube) and a detecting section provided across the cavity portion for detecting X-rays emitted from the X-ray generator.

In performing a scan, the subject is laid on the carrier apparatus and conveyed toward the cavity portion of the gantry apparatus. Then, the rotating section of the gantry apparatus is driven to rotate and at the same time the X-ray tube is driven, thereby emitting X-rays from different directions toward the subject, and detecting X-rays having passed through the subject by the detecting section. The operating console receives signals corresponding to the intensity of the transmitted X-rays transferred from the gantry apparatus, and arithmetically produces an image corresponding to the X-ray attenuation factors in a cross-section of the subject based on the signals. The image reproduced is generally referred to as an X-ray tomographic image, and the processing to reproduce the X-ray tomographic image is referred to as reconstruction of an X-ray tomographic image, or simply as reconstruction. Each pixel constituting the reconstructed X-ray tomographic image is a numerical value representing the magnitude of the X-ray attenuation factor (or the X-ray transmission factor), which value is generally referred to as a CT number.

Thus, the X-ray CT system can scan several regions such as the head, thorax (lungs) or abdomen of a subject, and is effectively used for diagnosis.

Although in some cases an X-ray tomographic image can be obtained which is high in contrast and easy to use in diagnosis, in other cases an X-ray tomographic image which is low in contrast and difficult to use in diagnosis is obtained, depending upon the measured region of the subject. Simply stated, the contrast can be conveniently considered as being low when all the pixels constituting an X-ray tomographic image have almost the same CT numbers, and being high when the CT numbers are considerably different from one another.

Low contrast is often found in X-ray tomographic images of the head of the subject. The reason of this is that the head, i.e., the brain, is largely composed of white matter and gray matter, resulting in almost identical CT numbers. On the other hand, an X-ray tomographic image of the abdomen has high contrast, and an image which is easy to use in diagnosis can be easily obtained.

SUMMARY OF THE INVENTION

The present invention was made to address such a problem, and is directed to providing an X-ray CT system, gantry apparatus, operating console and storage medium which enable an X-ray tomographic image to be obtained with high quality while minimizing the exposed dose to a subject by employing the most suitable filter according to the region of the subject to be scanned.

In order to solve such a problem, a gantry apparatus in an X-ray CT system of the present invention comprises, for example, a configuration as described below.

Specifically, there is provided a gantry apparatus in an X-ray CT system equipped with a gantry rotating section having an X-ray generating source and an X-ray detecting section for detecting X-rays emitted from the X-ray generating source across a cavity portion for positioning a subject, which gantry apparatus comprises a plurality of filters having different X-ray transmission properties, and positioning means for, when one of the plurality of filters is selected, positioning the selected filter at a position between the X-ray generating source and the X-ray detecting section in the proximity of the X-ray generating source.

According to a preferred embodiment of the present invention, the plurality of filters are provided in a single filter unit.

Moreover, the positioning means is preferably means for controlling a motor for moving the filter unit.

Moreover, the plurality of filters preferably include a first filter for scanning the head of the subject and a second filter for scanning the abdomen, and when the X-ray transmission factors of the first and second filters are represented as F1 and F2, respectively, the following relationship preferably holds:

$$F2<F1.$$

Furthermore, the plurality of filters preferably further include a third filter for use in scanning the thorax having an X-ray transmission factor of F3, and the following relationship holds:

$$F3<F2<F1.$$

Further, the thicknesses of the plurality of filters are preferably different.

Moreover, the gantry apparatus comprises means for connecting an operating console that supplies an instruction signal to the gantry apparatus and performs reconstruction processing for an X-ray tomographic image based on data transferred from the gantry apparatus, and the motor control means controls the motor according to instruction commands from the operating console.

The present invention also provides a method of controlling a gantry apparatus. Specifically, it provides a method of controlling a gantry apparatus in an X-ray CT system equipped with a gantry rotating section having an X-ray generating source and an X-ray detecting section for detecting X-rays emitted from the X-ray generating source across a cavity portion for positioning a subject, which method comprises a step of providing a plurality of filters having different X-ray transmission properties, and a positioning step of, when one of the plurality of filters is selected, positioning the selected filter at a position between the X-ray generating source and the X-ray detecting section in the proximity of the X-ray generating source.

In this method, the plurality of filters are preferably provided in a single filter unit.

Moreover, the positioning step is preferably a step of controlling a motor for moving the filter unit.

According to a preferred embodiment of the present invention, it is also an object thereof to provide an operating console connected to the above-described gantry apparatus.

The operating console is connected to the aforementioned gantry apparatus, supplies an instruction signal to the gantry apparatus and performs reconstruction processing for an X-ray tomographic image based on data transferred from the gantry apparatus, and the operating console comprises display means for displaying a menu for selecting a scan region of a subject, decision means for deciding which of the plurality of filters is to be employed based on the selected scan region, and means for supplying an instruction indicating the filter selection decided by the deciding means to the gantry apparatus.

According to a preferred embodiment of the present invention, the operating console comprises storage means for storing respective correction data corresponding to the plurality of filters incorporated in the gantry apparatus, and correction means for correcting data representing the result of a scan transferred from the gantry apparatus using correction data corresponding to the filter decided by the deciding means, and reconstructs an X-ray tomographic image using data corrected by the correction means.

Preferably, the display means further displays at least one field for inputting the size of the subject, and the deciding means decides a filter to be employed based on the input subject size and scan region.

The present invention also provides a method of controlling an operating console. Specifically, it provides a method of controlling an operating console that supplies an instruction signal to the aforementioned gantry apparatus and performs reconstruction processing for an X-ray tomographic image based on data transferred from the gantry apparatus, which method comprises a display step of displaying a menu for selecting a scan region of a subject, a decision step of deciding which of the plurality of filters is to be employed based on the selected scan region, and a step of supplying an instruction indicating the filter selection decided at the deciding step to the gantry apparatus.

Moreover, the present invention provides a storage medium for storing a program code for an operating console. Specifically, it provides a storage medium for storing a program code for an operating console that supplies an instruction signal to the aforementioned gantry apparatus and performs reconstruction processing for an X-ray tomographic image based on data transferred from the gantry apparatus, which storage medium stores a program code of a display step of displaying a menu for selecting a scan region of a subject, a program code of a decision step of deciding which of the plurality of filters is to be employed based on the selected scan region, and a program code of a step of supplying an instruction indicating the filter selection decided at the deciding step to the gantry apparatus.

Furthermore, the present invention provides an X-ray CT system. Specifically, it provides an X-ray CT system equipped with a gantry apparatus and an operating console, the gantry apparatus having an X-ray generating source and an X-ray detecting section for detecting X-rays emitted from the X-ray generating source across a cavity portion for positioning a subject, and the operating console supplying an instruction signal to the gantry apparatus and performing reconstruction processing for an X-ray tomographic image based on data transferred from the gantry apparatus, which gantry apparatus comprises a plurality of filters having different X-ray transmission properties, and positioning means for, when one of the plurality of filters is selected, positioning the selected filter at a position between the X-ray generating source and the X-ray detecting section in the proximity of the X-ray tube, and which operating console comprises display means for displaying X-ray generating source for selecting a scan region of a subject, decision means for deciding which of the plurality of filters is to be employed based on the selected scan region, and means for supplying an instruction indicating the filter selection decided by the deciding means to the gantry apparatus.

Preferably, the operating console further comprises storage means for storing respective correction data corresponding to the plurality of filters incorporated in the gantry apparatus and correction means for correcting data representing the result of a scan transferred from the gantry apparatus using correction data corresponding to the filter decided by the deciding means, and the operating console reconstructs an X-ray tomographic image using data corrected by the correction means.

Moreover, the display means preferably further displays at least one field for inputting the size of the subject, and the deciding means decides a filter to be employed based on the input subject size and scan region.

Moreover, the plurality of filters are preferably provided in a single filter unit.

Further, the positioning means is preferably means for controlling a motor for moving the filter unit.

Moreover, the plurality of filters preferably include a first filter for scanning the head of the subject and a second filter for scanning the abdomen, and when the X-ray transmission factors of the first and second filters are represented as F1 and F2, respectively, the following relationship holds:

$F2 < F1.$

Moreover, the plurality of filters preferably further include a third filter for use in scanning the thorax, having an X-ray transmission factor of F3, and the following relationship holds:

$F3 < F2 < F1.$

Moreover, the thicknesses of the plurality of filters are preferably different.

Moreover, the display means preferably further displays at least one field for inputting the size of the subject, and the deciding means decides a filter to be employed based on the input subject size and scan region.

According to the present invention as described above, an X-ray tomographic image can be obtained with high quality while minimizing the exposed dose to a subject by employing the most suitable filter according to the region of the subject to be scanned.

Further objects and advantages of the present invention will be apparent from the following description of the preferred embodiments of the invention as illustrated in the accompanying drawings.

DETAILED DESCRIPTION OF THE INVENTION

Embodiments of the present invention will now be described in detail with reference to the accompanying drawings.

Figure 1:
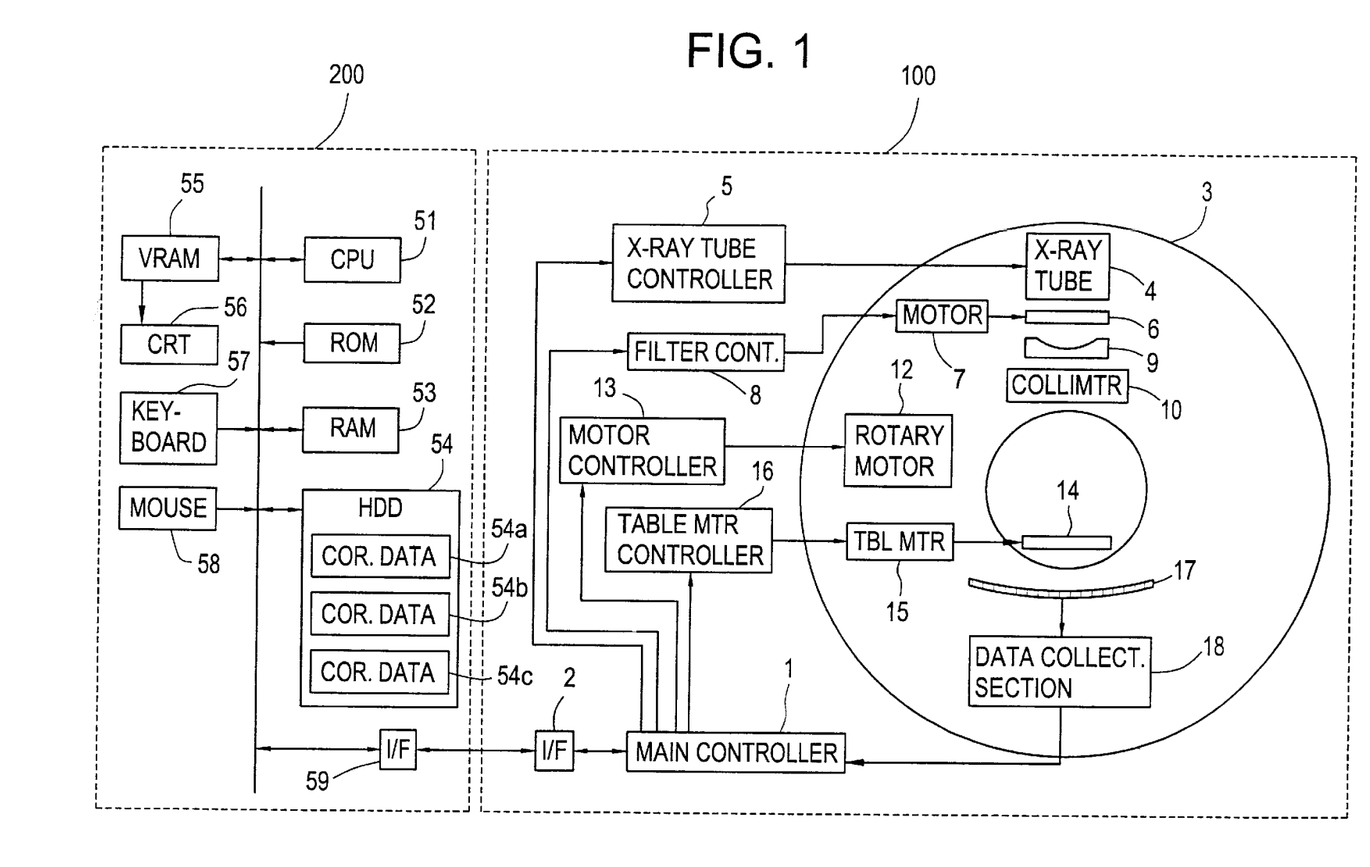
FIG. 1 is a configuration diagram of an X-ray CT system in one embodiment.

FIG. 1 is a block configuration diagram of an X-ray CT system in one embodiment. As shown, the system is comprised of a gantry apparatus for irradiating a subject with X-rays and detecting X-rays having passed through the subject, and an operating console 200 for performing several kinds of operating settings for the gantry apparatus 100, and reconstructing an X-ray tomographic image based on data output from the gantry apparatus 100 for display.

The gantry apparatus 100 comprises a main controller 1 for controlling the entire apparatus 100, and the following components.

Reference numeral 2 designates an interface for communicating with the operating console 200, and 3 designates a planar annular gantry having a cavity portion for carrying a subject (human subject) laid on a table 14 (in a direction perpendicular to the drawing's plane, which will be referred to as a Z-axis or a body axis hereinbelow). Reference numeral 4 designates an X-ray tube which is an X-ray generating source, and the X-ray tube 4 is driven and controlled by an X-ray tube controller 5. Reference numeral 6 designates a filter unit, which characterizes the present invention, and the filter unit 6 supports at least two types of filters which can be switched as desired in this embodiment. The particulars of the structure of the filter unit 6 and the filters supported thereon will be described in detail later. Reference numeral 7 designates a motor for switching between the filters of the filter unit 6, and 8 designates a filter controller for driving and controlling the motor 7.

Reference numeral 9 designates a filter (made of a material such as Teflon) in a shape having a thin central portion and thick end portions in order to reduce the X-ray attenuation at the central portion and enhance the X-ray attenuation at the end portions, which is generally known and referred to as a bow-tie filter. Reference numeral 10 designates a collimator having a slit for defining a range of X-ray irradiation. Reference numeral 12 designates a rotary motor for rotating the gantry 3, and 13 designates a motor controller for driving the rotary motor 12. Reference numeral 14 designates a table for resting the subject, 15 a table motor for carrying the table 14 in the Z-axis direction, and 16 a table motor controller for driving and controlling the table motor 15.

Reference numeral 17 designates an X-ray detecting section for detecting X-rays having passed through the subject, comprised of a detecting array in which about 1,000 X-ray detecting elements are arranged in a row. Some X-ray CT systems have a plurality of such detecting arrays. Such systems are called multi-slice X-ray CT systems. For brevity of description, the present invention will be described with reference to a single-slice X-ray CT system having only one detecting array, but it will be easily recognized that the present invention also applies to multi-slice X-ray CT systems.

Reference numeral 18 designates a data collecting section for collecting data obtained by the X-ray detecting section 17 and converting the data into digital data.

The operating console 200 is constituted by a "workstation," which comprises a CPU 51 for controlling the entire apparatus, a ROM 52 storing a boot program and BIOS, and a RAM 53 that serves as a main storage device, as shown, and the following components.

An HDD 54 is a hard disk device, which stores an OS, and a diagnosis program for supplying several kinds of instructions to the gantry apparatus 100 and reconstructing an X-ray tomographic image based on data received from the gantry apparatus 100. In addition, it stores correction data 54a–54c as shown (which will be described in detail later). A VRAM 55 is a memory for developing image data to be displayed, and the image data can be displayed on a CRT 56 by developing the image data and the like there. Reference numerals 57 and 58 designate a keyboard and a mouse, respectively, for performing several kinds of settings. Reference numeral 59 designates an interface for communicating with the gantry apparatus 100.

In performing a scan, and in the aforementioned configuration, an operator (technician or physician) operates the operating console to specify a region to be scanned in the subject, and thereafter prescribes a scan schedule in detail. Then, the operator gives a scan start instruction. A program running on the operating console in turn issues several control commands to the gantry apparatus 100 (main controller 1) according to the prescribed scan schedule. The main controller 1 on the gantry apparatus 100 supplies control signals to the X-ray tube controller 5, filter controller 8, collimator controller 11, motor controller 13 and table motor controller 16 according to the control instruction commands. Consequently, X-rays generated at the X-ray tube 4 and having passed through the subject can be detected by the X-ray detecting section 17, and the digital data of the X-rays can be obtained from the data collecting section 18. The main controller 1 transfers the data to the operating console 200 via the interface 2. Since the gantry 3 is rotated by the rotary motor 12 and the table 14 is also carried along the Z-axis, digital data of transmitted X-rays at different rotation angles and different Z-axis positions are sequentially transferred to the operating console 200.

One scanning technique which involves stopping the table 14 and fixing the table 14 at a certain Z-axis position, rotating the gantry 3 one time in this condition, and then carrying the table 14 to a next scan position and rotating the gantry 3 again, is called an axial scan; and another scanning technique which involves simultaneously rotating the gantry 3 and carrying the table 14 is called a helical scan. Either of the scanning techniques may be employed.

The program running on the operating console 200 then performs processing to reconstruct an X-ray tomographic image by a known processing method based on the received data, and sequentially displays the results on the CRT 56.

<<Description of the Filter Unit>>

X-rays generated from the X-ray tube 4 have a continuous spectral distribution, rather than a specific wavelength of X-rays (line spectrum). The lower-energy (longer-wavelength) X-rays in those X-rays tend to be absorbed by the subject, while the higher-energy (shorter-wavelength) X-rays tend to be transmitted. That is, when X-rays having a continuous spectrum are applied to the subject, there is a tendency for only the high-energy X-rays to be transmitted through the subject. This phenomenon is generally referred to as the beam-hardening effect of X-rays.

Since the X-rays transmitted through the subject are high-energy X-rays, it is desired that no low-energy X-rays be applied to the subject from the beginning.

Therefore, it has been made mandatory to provide a filter having a thickness of at least 2.5 mm in aluminum equivalent between the X-ray tube and the subject, rather than directly applying the X-rays generated from the X-ray tube 4. By passing the X-rays through a filter having such a property, lower-energy X-rays can be attenuated by the filter, thereby preventing the subject from being exposed to unnecessary radiation.

However, there is room for further improvement on this technique in which a scan is performed using only one filter having a thickness of 2.5 mm in aluminum equivalent. The reason of this is as follows.

As described earlier when X-rays having a continuous spectrum are applied to the subject, lower-energy X-rays are absorbed by the subject in a larger proportion. Since the abdomen of the subject is the region having the largest cross section, X-rays that reach the X-ray detecting section 17 mostly have a high energy in scanning such a region. Thus, when a scan is performed on the abdomen, the beam-hardening effect is most prominent. Therefore, a filter having a thickness of more than 2.5 mm in aluminum equivalent may safely be used in scanning the abdomen.

On the other hand, the head of the subject has a smaller cross section than the abdomen, resulting in a smaller beam-hardening effect. Moreover, since the brain is largely composed of white matter and gray matter and, in addition, the difference in CT value between them is small, it is difficult to reconstruct an X-ray tomographic image having a sufficient contrast.

To enhance the contrast of an X-ray tomographic image, it is necessary to make more X-rays reach the X-ray detecting section 17, and to increase the S/N ratio.

Therefore, in scanning the head of the subject, it is desired that a thinner filter (but not less than 2.5 mm in aluminum equivalent) than that used in scanning the abdomen be used.

In scanning the thorax, since the lungs are hollow and the contrast that depends upon the existence of the subject's tissue is high from the start, an X-ray tomographic image can be reconstructed with a sufficiently high quality using only high-energy X-rays. Therefore, for a filter employed in scanning the thorax, a thicker filter (a filter having a higher attenuation factor) than for the abdomen can be used, thereby cutting low-energy X-rays applied to the subject to prevent unnecessary radiation exposure.

In summary, when the thicknesses of filters used in scanning the head, abdomen and thorax are represented as Ta, Tb and Tc, in aluminum equivalent, the following relationship holds:

$$2.5 \text{ mm} \leq Ta < Tb < Tc.$$

Consequently, a scan for obtaining signals having a sufficient S/N ratio can be performed according to the scan region, and yet the exposure to the subject can be decreased to the minimum required amount.

The filter thicknesses for particular regions are desirably as follows:

the filter thickness Ta for the head: 2.5–3.5 mm in aluminum equivalent, the filter thickness Tb for the abdomen: 6.0–8.0 mm in aluminum equivalent, and the filter thickness Tc for the thorax: 10.0–12.0 mm in aluminum equivalent.

Although aluminum is taken as a standard here, if copper is to be used, the thickness may be 0.2 mm for the abdomen and 0.25 mm for the thorax, for example.

Figure 2:
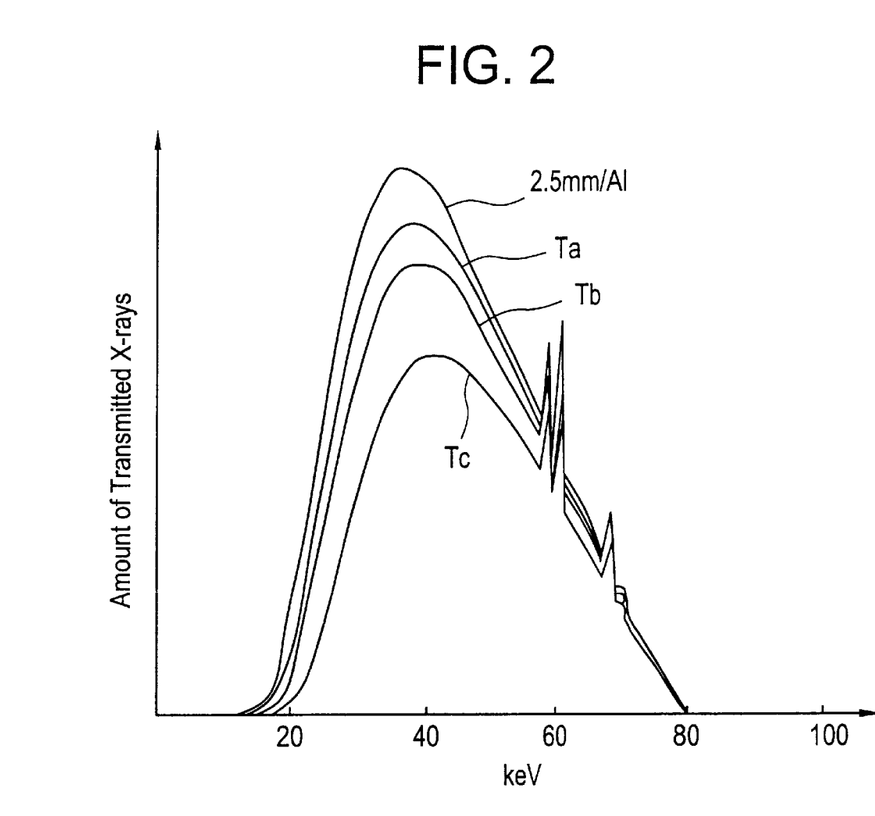
FIG. 2 is a diagram illustrating the properties of filters used in the embodiment.

FIG. 2 illustrates an X-ray transmission spectrum distribution in using these filters. It will be recognized that the spectrum of transmitted X-rays is shifted toward higher energy with the increasing filter thickness, although the amount of transmitted X-rays tends to decrease.

Figure 3:
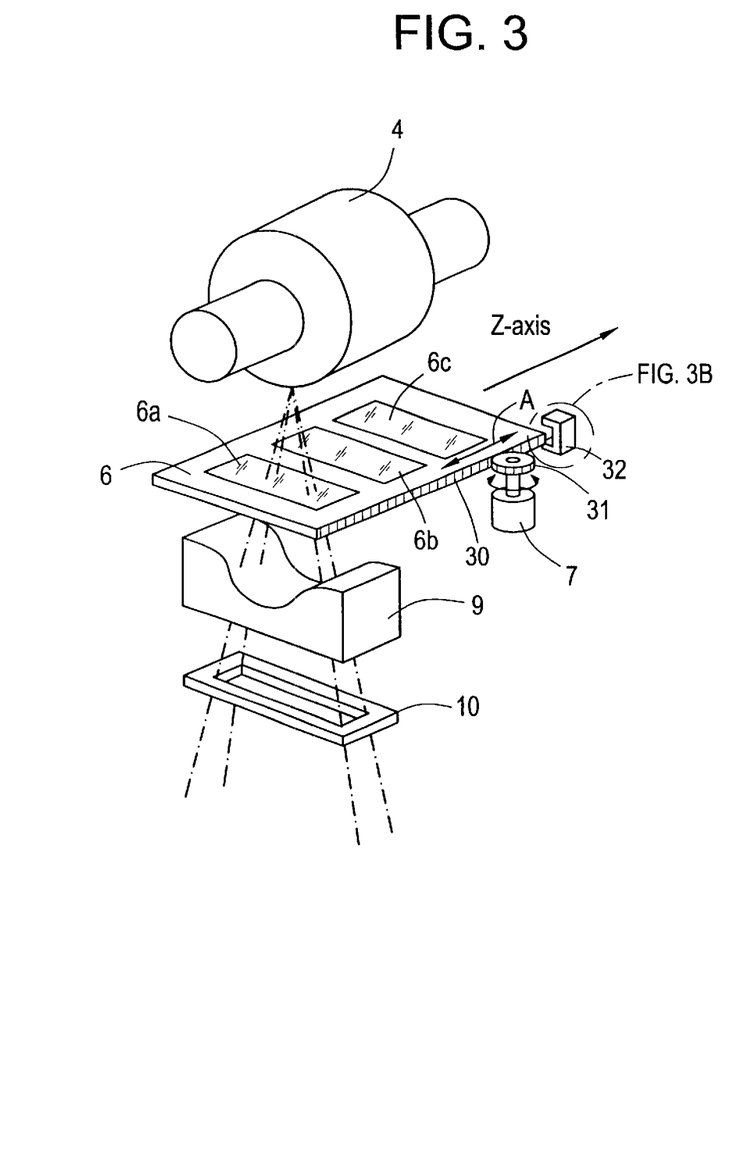
FIG. 3 is a perspective view illustrating the structure around a filter unit in the embodiment.
Figure 3B:
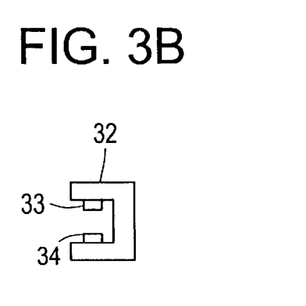

FIG. 3 is a perspective view of the configuration around the filter unit 6 in the present embodiment. As shown, the filter unit 6 supports three filters 6a, 6b and 6c (having respective thicknesses of Ta, Tb and Tc) provided slidably in the subject-carrying direction (Z-axis). The filter unit 6 is provided on its side with teeth 30, with which a gear 31 secured to a driving spindle of the motor 7 engages, as shown. The gear 31 is rotated by driving the motor 7, so that the position of the filter unit 6 can be changed freely along arrow A (Z-axis) in the drawing.

Reference numeral 32 designates a sensor comprising a light-emitting element 33 and a light-receiving element 34 at the illustrated positions. When the gantry apparatus 100 is activated, the main controller 1 supplies a drive control signal for the motor 7 to the filter unit controller 8 to move the filter unit 6, and determines a home position of the filter unit 6 as the point where the light-receiving element 34 changes from a state incapable of detecting a light from the light-emitting element 33 into a state capable of detecting the light (or vice versa). By counting the number of pulses supplied to the motor 7 starting with the home position, the position of the filter unit 6 is identified. Thus, a desired one of the filters 6a–6c can be positioned just below the X-ray tube 4.

After the initialization processing for the activation as described above, the main controller 1 selects the most suitable filter by issuing a control command to the filter controller 8 according to an instruction command from the operating console 200. For example, when a selection command that means the filter 6c is to be employed is received from the operating console 200, a shift amount with respect to the current position is calculated, and a control signal corresponding to the amount is supplied to the motor controller 8 to enable a scan employing the filter 6c.

<<Control of a Scan>>

Figure 4:
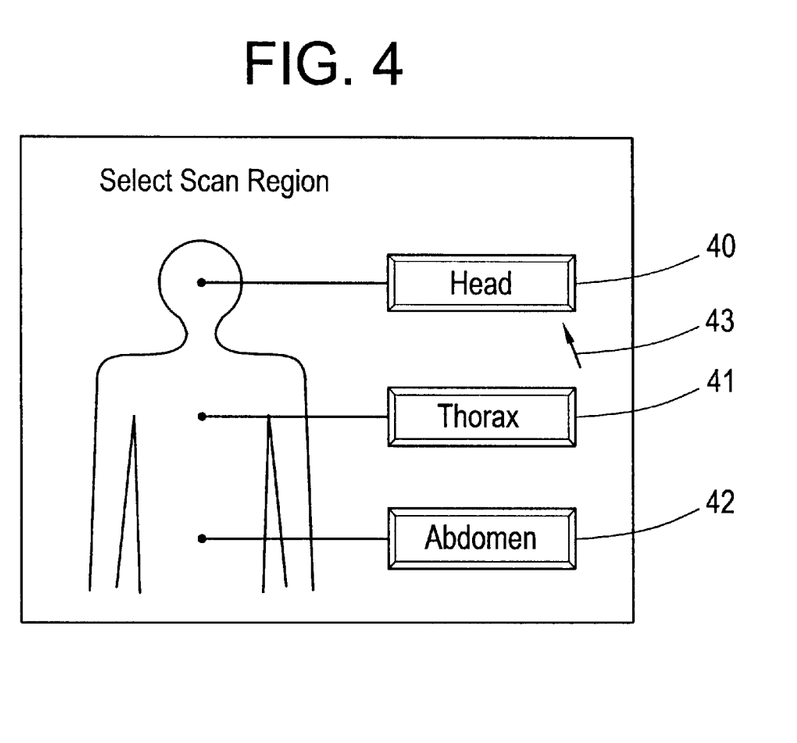
FIG. 4 is a view illustrating an example of a measured region selection screen in the embodiment.

FIG. 4 illustrates a start menu for scan scheduling displayed on the CRT 56 of the operating console 200.

As shown, a model image is displayed on the left of the screen, and logical buttons 40–42 are displayed on the right for determining the region to be scanned. The selection of one of the buttons is achieved by moving a cursor 43 linked to the mouse 58 to a desired button and clicking a button on the mouse 58.

Upon clicking any one of the buttons 42–44, the CPU 51 outputs a filter selection command corresponding to the selected region to the gantry apparatus 100 via the interface 59. Thereafter, the main controller 1 in the gantry apparatus 100 interprets the received command, and issues a control command to the filter controller 8 based on the received command, as described earlier.

Then, a detailed scan schedule for the selected region will be specified on the operating console 200. However, since this process has no direct relation with the present invention and is a known procedure, a detailed description will be omitted.

Since the filters 6a–6c have different transmission properties (or attenuation properties), as shown in FIG. 2, the electric signal output from the X-ray detecting section 17 is naturally one affected by filter employed. Specifically, even if the same region of the subject is scanned, the signal obtained employing the filter 6a is different from the signal obtained employing the filter 6b.

Therefore, the operating console 200 is required to perform reconstruction processing for an X-ray tomographic image suited to the filter employed during the scan by the gantry apparatus 100. Therefore, respective correction data corresponding to the filters 6a–6c to be employed are stored in the HDD 54 of the operating console 200. When the region to be measured has been determined, the appropriate correction data selected from among the correction data 54a–54c is used to correct data transferred from the gantry apparatus 100, and thereafter, the reconstruction processing for an X-ray tomographic image is performed. It should be noted that the correction data 54a–54c also take the properties of the bow-tie filter 9 into account.

Figure 5:
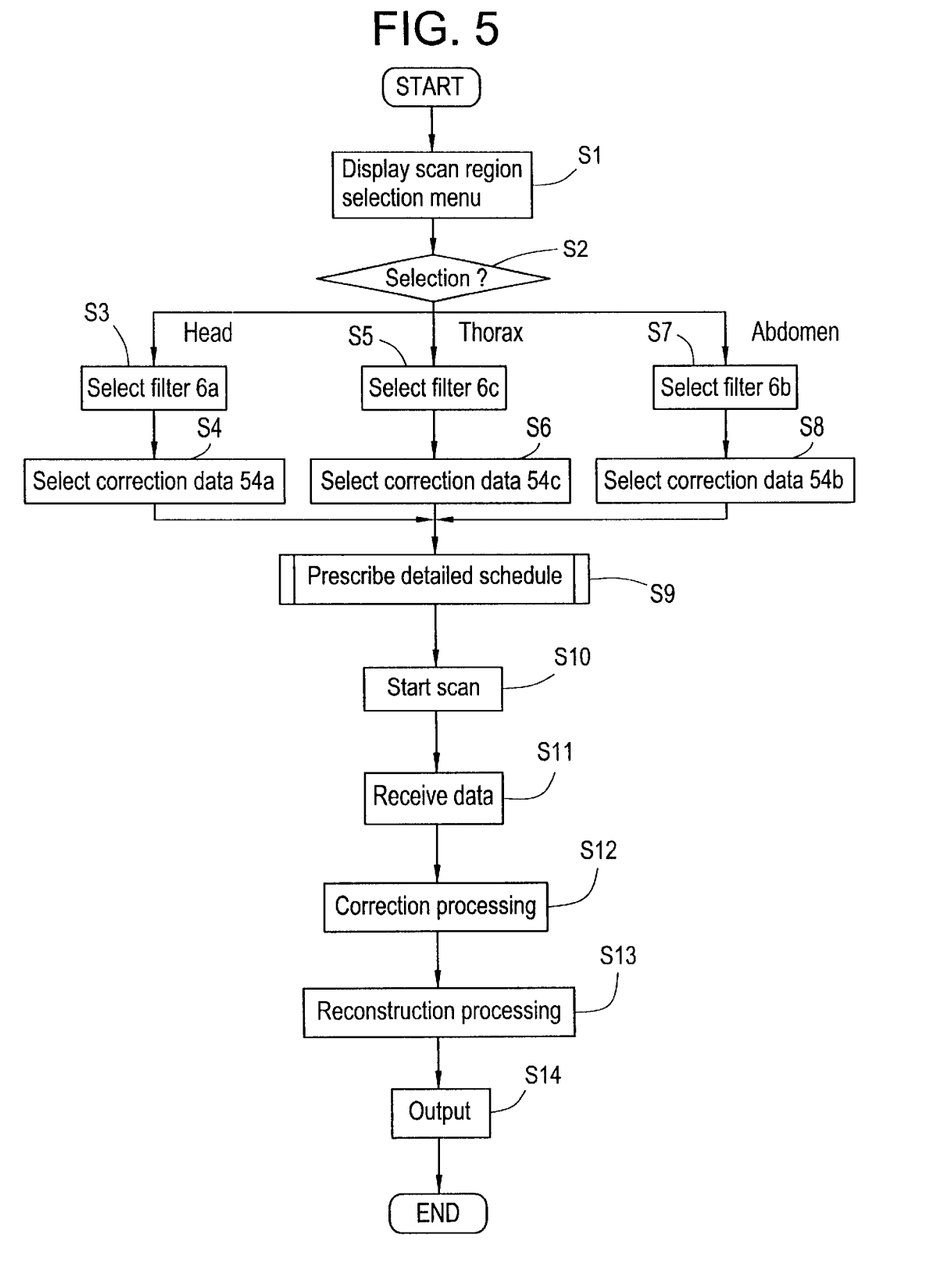
FIG. 5 is a flow chart illustrating a processing procedure running on an operating console in the embodiment.

In summary, the CPU 51 of the operating console 200 is operated according to the flow chart shown in FIG. 5. This program is previously stored in the HDD 54, and is loaded into the RAM 53 for execution.

First, at Step S1, the scan region selection screen is displayed as shown in FIG. 4, and the operator (technician or physician) is prompted to select which region is to be scanned. After the selection, a decision is made on which region was selected at Step S2.

If the head was selected as the scanned object, the process goes to Step S3 and an instruction command for the filter 6a selection is issued to the gantry apparatus 100 to employ the filter 6a. Then, the gantry apparatus 100 controls the movement of the filter unit 6 as described earlier, positions the specified filter just below the X-ray tube 4 and fixes the filter at that position. Then, the process goes to Step S4 to select the correction data 54a for the filter 6a and reads the data 54a out to a predefined region in the RAM 53.

If the thorax was selected as the scanned object, an instruction command for the filter 6c selection is issued at Step S5, the correction data 54c for the filter 6c is selected at Step S6, and the data 54c is read out to a predefined region in the RAM 53.

If the abdomen was selected as the scanned object, an instruction command for the filter 6b selection is issued at Step S7, the correction data 54b for the filter 6b is selected at Step S8, and the data 54b is read out to a predefined region in the RAM 53.

In any case, the process goes to Step S9, and a detailed scan schedule is prescribed for the selected scan region. The prescription includes, for example, items about the range of the carrying direction to be scanned (from which position to which position), about which interval is to be selected for reconstructed X-ray tomographic images, and the like. These items are known and a description thereof will be omitted.

Then, at Step S10, when the operator orders a scan to be started, processing are carried out to transfer several kinds of control commands to the gantry apparatus 100 according to the scan schedule, and to cause the gantry apparatus 100 to control the driving operations of the motor controller 13, table motor controller 16 and X-ray tube controller 5 according to the supplied commands, and to transfer X-ray transmission data collected by the data collecting section 18 (data from all the channels in the X-ray detecting section 17) to the operating console.

The operating console 200 receives the data transferred from the gantry apparatus 100 at Step S11. The process then goes to Step S12, and the correction data previously read out to the RAM 53 is used to perform correction processing on the received data. Then, at Step S13, known processing for reconstruction of an X-ray tomographic image is executed, and processing for outputting the image (display processing etc.) is executed at Step S14.

According to the present embodiment as described above, by employing the most suitable filter corresponding to the region to be measured in a subject, the subject is only exposed to the minimum required radiation and the quality of the reconstructed X-ray tomographic image can be improved.

<<Second Embodiment>>

Although the filter to be employed is determined according to the region to be measured in the former embodiment, the size of subjects widely varies. Especially, the cross-sectional area of the abdomen is different among individuals. For example, a scan of the abdomen of a large person exhibits a more prominent hardening effect than that of a thin person. The same is true for an adult and a child.

Therefore, in this second embodiment, the parameters for determining the filter to be employed additionally include the size of the subject, as well as the region to be measured. It should be noted that the number of types of filters should be increased as compared with the first embodiment because the size of the subject is additionally considered.

Figure 6:
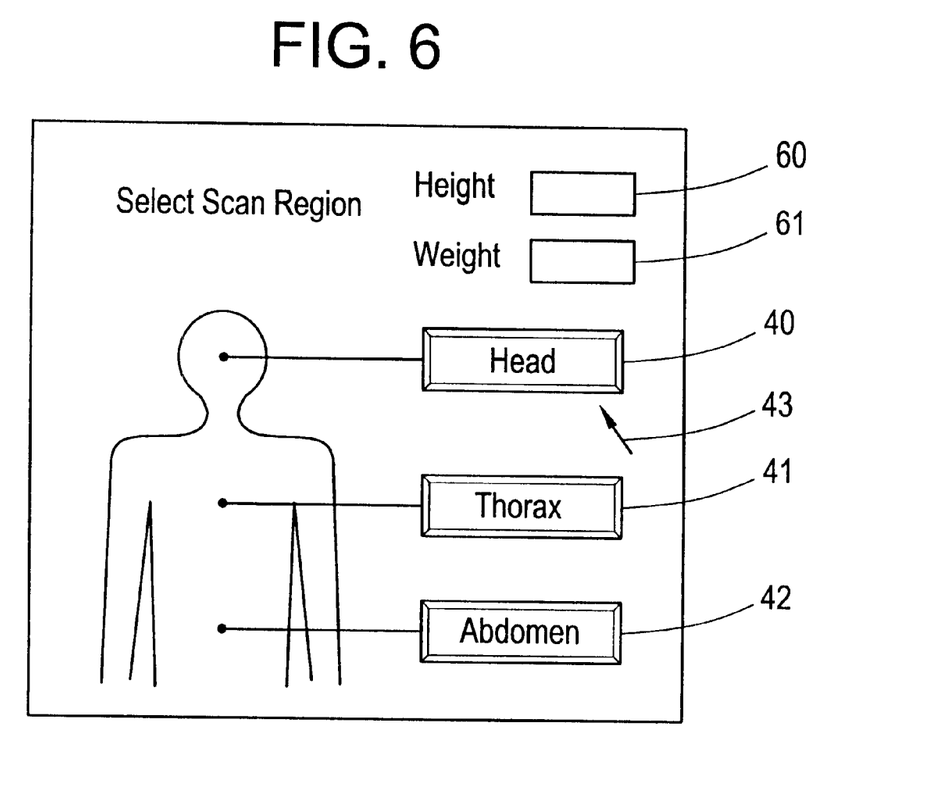
FIG. 6 is a view illustrating another example of the measured region selection screen in a second embodiment.

FIG. 6 shows a measured region selection screen in accordance with the second embodiment. As shown, fields 60 and 61 are provided for inputting the height and weight as the size of a subject.

Figure 7:
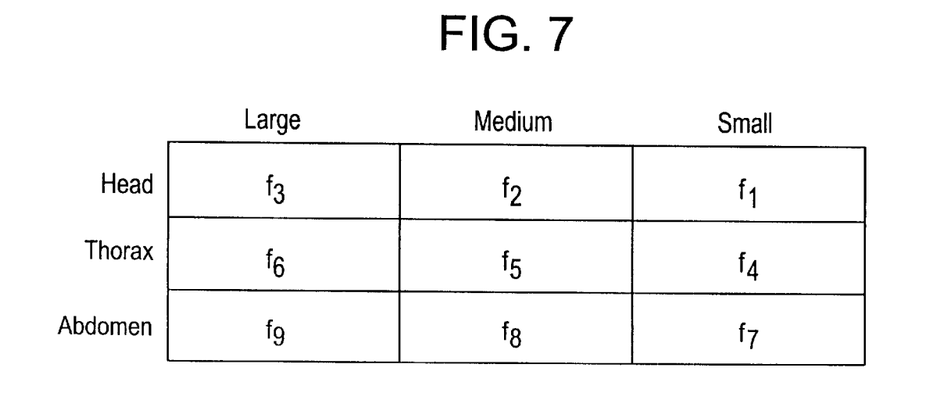
FIG. 7 is a diagram illustrating a filter selection table in the second embodiment.

If the size of a subject is assumed to be classified into, for example, three grades: large, medium and small, since the number of the measured region is also three, nine filters at maximum may be needed. Assume that the filters are represented as f1, f2, . . . , f9.

The operator first inputs the height and weight of a subject to be scanned, and then performs the operation to select the region to be measured. Consequently, an appropriate filter is determined from among the filters f1, f2, . . . , f9, and an instruction command for the filter selection is sent to the gantry apparatus 100. It will be easily recognized that the HDD 54 on the operating console 200 is provided with the same number of correction data sets as the number of filters.

In determining the filter to be employed, a table as exemplarily shown in FIG. 7 may be stored in the HDD 54 to select the filter with reference thereto.

As a result, since the filter to be employed can be determined additionally considering the size of the subject, the exposed dose to the subject is further reduced, and an X-ray tomographic image can be reconstructed with high accuracy.

It should be noted that although only one example is described of the switching structure of the filter unit of the gantry apparatus 100 for the first and second embodiments, other structures may be contemplated. The point is that it should be possible to perform a scan employing a desired filter from among filters having different transmission properties.

Moreover, although the regions to be scanned have been described as three regions: the head, thorax and abdomen in the above embodiments, the minimum requirement is two regions: the head and abdomen. Moreover, the regions to be measured may include four regions or more for fine definition.

Moreover, although the filter in the embodiments is described as being made of aluminum, there is no limitation on the material. The point is that filters having transmission properties like those shown in FIG. 2 should be used, and other materials such as copper or the like may be employed.

Furthermore, the present invention is not limited to the apparatuses and methods for implementing the aforementioned embodiments, but the scope of the present invention includes the case in which the aforementioned embodiments are achieved by a software program code supplied to a computer (CPU or MPU) in the aforementioned system or apparatus, and the computer of the system or apparatus operates the several devices according to the program code.

In this case, the software program code per se is regarded as achieving the functions of the embodiments. Therefore, the program code per se, and means, particularly, a storage medium storing the program code, for supplying the program code to the computer are contained within the scope of the present invention.

For the storage medium for storing such a program code, a floppy disk, hard disk, optical disk, magneto-optical disk, CD-ROM, magnetic tape, non-volatile memory card, ROM or the like may be employed, for example. Furthermore, the program code may be downloaded via a medium that is a network (e.g., the Internet).

Many widely different embodiments of the invention may be configured without departing from the spirit and the scope of the present invention. It should be understood that the present invention is not limited to the specific embodiments described in the specification, except as defined in the appended claims.

What is claimed is:

1. A system for controlling X-ray beams in an X-ray CT system having an X-ray generating source, an X-ray detecting section, a first filter unit disposed closest to said detecting section, and a second filter unit disposed closest to said source and between said source and said first filter unit, said first filter unit having a thin central portion and thick end portions to reduce X-ray attentuation at said central portion and enhance X-ray attenuation at the end portions, wherein said second filter unit is a flat plate having therein at least two filters, each having different X-ray transmission properties; and further comprising positioning means for selectively moving said second filter unit so that said X-ray beams are selectively directed through a selected one of said at least two filters and then through said first filter unit.

2. The system of claim 1, wherein said positioning means comprises a motor, and a gear attached to an edge of said flat plate of said second filter unit, and means for energizing said motor and engaging said gear to selectively drive said flat plate and cause a selected one of said at least two filters of said second filter unit to filter said X-ray beams.

3. The system of claim 1, wherein one of said at least two filters of said second filter unit is used to scan a head of a subject, and a second of said at least two two filters of said second filter unit is used to scan an abdomen of said subject, and wherein said first and second filters of said second filter unit have X-ray transmission factors F1 and F2, respectively, with F2 being less than F1.

4. The system of claim 3, wherein said second filter unit further comprises a third filter for use in scanning a thorax of said subject, said third filter having an X-ray transmission factor F3 which is less than X-ray transmission factor F2.

5. The system of claim 4, wherein said first, second, and third filters of said second filter unit have different thicknesses.

6. The system of claim 1, further comprising an operating means for supplying instruction signals to said source, said detecting section, and said positioning means to perform reconstruction processing for an X-ray tomographic signal based on data obtained from X-ray beams supplied through said first and second filter units and detected by said detecting section.

7. The system of claim 6, wherein said operating means comprises:

display means for displaying a menu for selecting a scan region of a subject, and at least one field for inputting size of said subject;

decision means for deciding which of said at least two filters of said second filter unit is to be used based on the selected scan region and input size of said subject; and means for supplying an instruction indicating the filter selection decided by said decision means to said positioning means.

8. The system of claim 7, further comprising:

storage means for storing respective correction data corresponding to said at least two filters of said second filter unit;

correction means for correcting data represent result of a scan transferred using correction data corresponding to the filter decided by said decision means; and wherein said operating means causes reconstitution of an X-ray tomographic image using data corrected by said correction means.

9. A method for controlling X-ray beams in an X-ray cT system having an X-ray generating source, an X-ray detecting section, a first filter unit disposed closest to said detecting section, and a second filter unit disposed closest to said source and between said source and said first filter unit, said first filter unit having a thin central portion and thick end portions to reduce X-ray attenuation at said central portion and enhance X-ray attenuation at the end portions, wherein said method comprises the steps of:

providing as said second filter unit a flat plate having therein at least two filters, each having different X-ray transmission properties; and selectively moving said second filter unit while keeping said first filter unit fixed so that said X-ray beams are selectively directed through a selected one of said at least two filters of said second filter unit and then through said first filter unit.

10. The method of claim 9, comprising the steps of:

providing said positioning means with a motor and a gear attached to an edge of said flat plate of said second filter unit; and engaging said motor to said gear to selectively drive said flat plate and cause a selected one of said at least two filters of said second filter unit to filter said X-ray beams.

11. The method of claim 9, further comprising the steps of:

providing said first and second filter units with X-ray transmission factors F1 and F2 respectively, with F2 being less than F1;

using one of said at least two filters of said second filter unit to scan a head of a subject; and using a second of said at least two filters of said second filter unit to scan an abdomen of said subject.

12. The method of claim 11, further comprising the steps of:

providing said second filter unit with a third filter having an X-ray transmission factor F3 which is less than F2; and scanning a thorax of said subject using said third filter.

13. The method of claim 12, wherein said first, second and third filters of said second filter unit have different thicknesses.

14. The method of claim 9, further comprising the steps of;

supplying instruction signals to said source, said detecting section, and said positioning means;

performing reconstruction processing for an X-ray tomographic signal based on data obtained from X-ray beams supplied through said first and second filter units and detected by said detecting section.

15. The method of claim 14, further comprising the steps of:

displaying a menu for selecting a scan region of a subject, and at least one field for inputting size of said subject;

deciding which of said at least two filters of said second filter unit is to be used based on the selected region and input size of said subject; and supplying an instruction indicating the filter selection decided by said deciding step to said positioning step.

16. The method of claim 15, further comprising the steps of:

storing respective correction data correspond to said at least two filters of said second filter unit;

correcting data representing result of scan transferred using correction data to the filter decided by said deciding step; and causing reconstruction of an X-ray tomographic image using data corrected by said correcting step.

17. A storage medium for storing a program code for providing instruction signals to a system for controlling X-ray beams in an X-ray CT system having an X-ray generating source, an X-ray detecting section, an operating device, a first filter unit disposed closest to said detecting section, and a second filter unit disposed closest to said source and between said source and said first filter unit, said first filter unit having a thin central portion and thick end portions to reduce X-ray attentuation at said center 1 portion and enhance X-ray attentuation at the end portions, wherein said second filter unit is a flat plate having therein at least two filters, each having different X-ray transmission properties; and positioning means for selectively moving said second filter unit so that said X-ray beams are selectively directed through a selected one of said at least two filters and then through said first filter unit, wherein said CT system performs reconstruction processing for an X-ray tomographic image based on data transferred from said detecting section, said storage medium storing a program code of a display step of displaying a menu for selecting a scan region of a subject, a program code of a decision step of deciding which of said at least two filters is to be used based on a selected scan region, and a program code of a step of supplying an instruction indicating the filter which is selected at said deciding step.

* * * * *